US008170302B1

(12) United States Patent
Gleason et al.

(10) Patent No.: US 8,170,302 B1
(45) Date of Patent: May 1, 2012

(54) SYSTEM AND METHOD FOR GENERATING MOTION CORRECTED TOMOGRAPHIC IMAGES

(75) Inventors: Shaun S. Gleason, Knoxville, TN (US); James S. Goddard, Jr., Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1058 days.

(21) Appl. No.: 11/241,359

(22) Filed: Sep. 30, 2005

(51) Int. Cl.
*G06K 9/00* (2006.01)
*A61B 6/00* (2006.01)
(52) U.S. Cl. .................... 382/128; 378/4; 382/131
(58) Field of Classification Search .......... 382/131; 378/4
See application file for complete search history.

(56) References Cited

U.S. PATENT DOCUMENTS

| | | | |
|---|---|---|---|
| 6,473,636 B1 | 10/2002 | Wei et al. | |
| 6,615,063 B1* | 9/2003 | Ntziachristos et al. | 600/312 |
| 7,310,443 B1* | 12/2007 | Kris et al. | 382/167 |
| 2005/0232477 A1* | 10/2005 | Sugihara et al. | 382/149 |

OTHER PUBLICATIONS

Gleason, S.S.; Goddard, J.S.; Paulus, M.J.; Baba, J.S.; Majewski, S.; Smith, M.; Tran, T.; Weisenberger, A.; Welch, B.; Wojcik, R., "Real-time, high-accuracy 3D tracking of small animals for motion-corrected SPECT imaging," Nuclear Science Symposium Conference Record, 2004 IEEE , vol. 5, no., pp. 3338-3342 vol. 5, Oct. 16-22, 2004.*
Goddard, J.S.; Gleason, S.S.; Paulus, M.J.; Kerekes, R.; Majewski, S.; Popov, V.; Smith, M.; Weisenberger, A.; Welch, B.; Wojcik, R., "Pose measurement and tracking system for motion-correction of unrestrained small animal PET/SPECT imaging," Nuclear Science Symposium Conference Record, 2003 IEEE , vol. 3, no., pp. 1824-1827 vol. 3, Oct. 19-25, 2003.*
Weisenberger, A.G.; Kross, B.; Gleason, S.S.; Goddard, J.; Majewski, S.; Meikle, S.R.; Paulus, M.J.; Pomper, M.; Popov, V.; Smith, M.F.; Welch, B.L.; Wojcik, R., "Development and testing of a restraint free small animal SPECT imaging system with infrared based motion tracking," Nuclear Science Symposium Conference Record, 2003 IEEE , vol. 3, no., pp.*
Goddard, J.S.; Gleason, S.S.; Paulus, M.J.; Kerekes, R.; Majewski, S.; Popov, V.; Smith, M.; Weisenberger, A.; Welch, B.; Wojcik, R., "Pose measurement and tracking system for motion-correction of unrestrained small animal PET/SPECT imaging," Nuclear Science Symposium Conference Record, 2003 IEEE, vol. 3, no., p. 1824-1827 vol. 3, Oct. 19-25, 2003.*
Goddard, J.S.; Gleason, S.S.; Paulus, M.J.; Majewski, S.; Popov, V.; Smith, M.; Weisenberger, A.; Welch, B.; Wojcik, R., "Real-time landmark-based unrestrained animal tracking system for motion-corrected PET/SPECT imaging," Nuclear Science Symposium Conference Record, 2002 IEEE , vol. 3, no., pp. 1534-1537 vol. 3, Nov. 10-16, 2002.*

(Continued)

*Primary Examiner* — Bhavesh Mehta
*Assistant Examiner* — Nirav G Patel
(74) *Attorney, Agent, or Firm* — Novak Druce + Quigg LLP

(57) ABSTRACT

A method and related system for generating motion corrected tomographic images includes the steps of illuminating a region of interest (ROI) to be imaged being part of an unrestrained live subject and having at least three spaced apart optical markers thereon. Simultaneous images are acquired from a first and a second camera of the markers from different angles. Motion data comprising 3D position and orientation of the markers relative to an initial reference position is then calculated. Motion corrected tomographic data obtained from the ROI using the motion data is then obtained, where motion corrected tomographic images obtained therefrom.

13 Claims, 2 Drawing Sheets

OTHER PUBLICATIONS

Horn, B. "Closed-form solution of absolute orientation using unit quaternions", 1987, Opt. Soc. Am. A., 4(4):629-642.

Weisenberger, et al "Instrumentation Development of a SPECT-CT system to Image Awake Mice", 1987, Opt. Soc. Am. A., 4(4):629-642.

Baba, et al "Application of Polarization for Optical Motion-Registered SPECT Functional Imaging of Tumors in Mice", Optical Diagnostics and Sensing V. Edited by Priezzhev, Alexander V.; Cote, Gerard L. Proceedings of the SPIE, vol. 5702, pp. 97-103 (Mar. 2005).

Weisenberger, et al "A Restraint-Free Small Animal SPECT Imaging System With Motion Tracking", 2005, IEEE Transactions on Nuclear Science, vol. 52, No. 3: 638-644 (Jun. 2005).

Kerekes, et al "Two Methods for Tracking Small Animals in SPECT Imaging", Sixth International Conference on Quality Control by Artificial Vision, Edited by Tobin, Kenneth W., Jr.; Meriaudeau, Fabrice. Proceedings of the SPIE, vol. 5132, pp. 129-139 (2003).

Weisenberger, et al, "Dual Low Profile Detector Heads for a Restraint Free Small Animal SPECT Imaging System", Nuclear Science Symposium Conference Record, 2004 IEEE Publication, vol. 4, Issue , 16-22, pp. 2456-2460 (Oct. 2004 ).

* cited by examiner

SYSTEM AND METHOD FOR GENERATING MOTION CORRECTED TOMOGRAPHIC IMAGES

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

CROSS-REFERENCE TO RELATED APPLICATIONS

Not applicable.

BACKGROUND OF THE INVENTION

Patient motion or motion of a living subject during imaging can cause image artifacts. The sources of motion can vary, including from restlessness, through respiration and heart beating, to small movements due to pressure changes over the cardiac cycle. In some cases motion artifacts degrade the diagnostic value of an image.

Optical methods including stereo methods for 3D measurements are known and are used to measure marker 3D position and orientation in medical imaging applications for motion correction. Generally, the patient is immobilized to limit motion during imaging. Existing measurement systems and related methods are not designed for fast motion measurement and correction.

Efficient methods for testing new drugs are very important to the pharmaceutical industry. The ability to screen test subjects for effects of a particular drug is an essential element in the process of product development. Small animals are essential for pharmaceutical testing, and mice in particular are useful for modeling human diseases. Efforts to scale down clinical medical imaging systems for smaller subjects have allowed medical researchers to obtain high-resolution computed tomography (CT) images of small animals for disease studies. Noninvasive imaging techniques, such as X-ray CT and positron emission tomography (PET), have been developed for small animal medical imaging applications. For example, small animal imaging is used in cancer research to monitor tumor growth and regression in mice.

While anatomical models are useful for studying drug effectiveness, it is very often desirable to screen test subjects for physiological effects of a drug. PET and single photon emission computed tomography (SPECT) are among current techniques used for functional medical imaging. Because test subjects must be kept alive during the screening process in order to monitor functional processes, either the animal must remain motionless for the duration of the scan or its movements must be measured and recorded with a high degree of precision and accuracy. Although sedation and physical restraint can be used to impede animal motion for this type of medical scan, both methods have the potential to alter the neurological and physiological processes that are being studied. Unrestrained awake animals tend to sometimes move rapidly. Unfortunately, as noted above, existing measurement systems are not designed for fast motion measurement and correction.

BRIEF DESCRIPTION OF THE DRAWINGS

A fuller understanding of the present invention and the features and benefits thereof will be obtained upon review of the following detailed description together with the accompanying drawings, in which:

FIG. 3(a) shows a scanned image of a mouse fitted with three optical retro reflective markers on its head in a burrow, while

SUMMARY OF THE INVENTION

Figure 1:
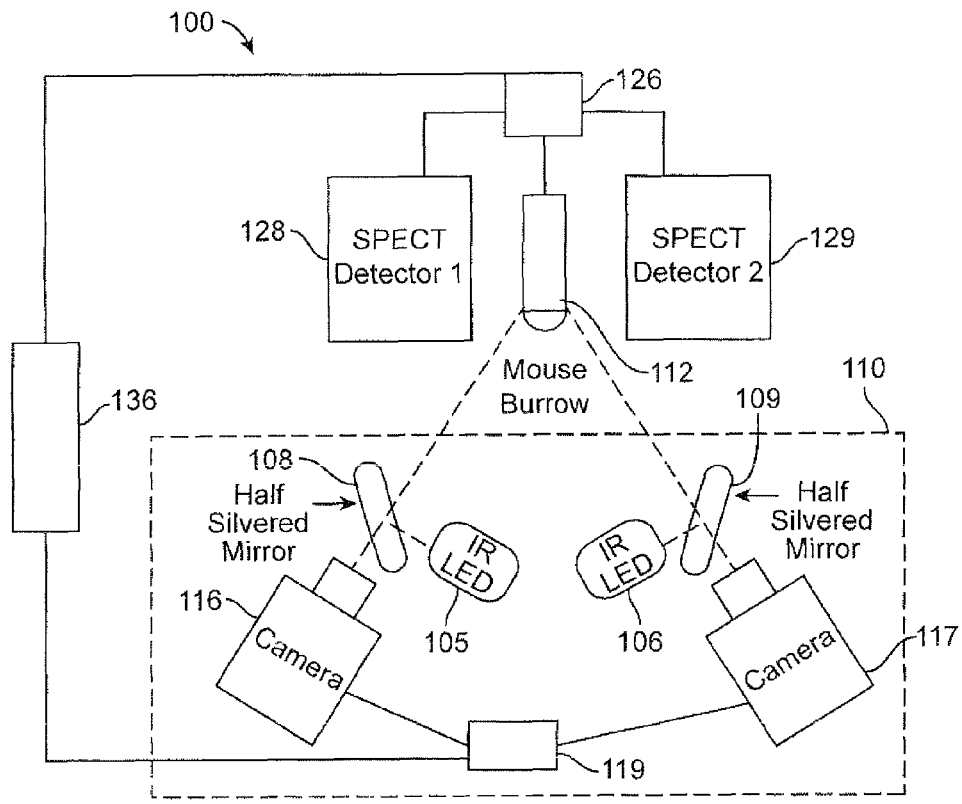
FIG. 1 is a schematic diagram of an exemplary motion correcting single photon emission computed tomography (SPECT) imaging system 100.

A method and related system for generating motion corrected tomographic images includes the steps of illuminating a region of interest (ROI) to be imaged being part of an unrestrained live subject and having at least three spaced apart optical markers thereon. Simultaneous images are acquired from a first and a second camera of the markers from different angles. Motion data comprising 3D position and orientation of the markers relative to an initial reference position is then calculated. Motion corrected tomographic data obtained from the ROI using the motion data is then obtained, where motion corrected tomographic images obtained therefrom. In one embodiment, the ROI is provided by an unrestrained awake animal. The unrestrained animal can be disposed in an confinement volume which is optically transparent to a wavelength of radiation used for the illuminating.

The tomographic images can be single photon emission computed tomography (SPECT) images. The markers are preferably retro-reflective and the illuminating is preferably aligned to be coaxial with an optical axis of the first and the second camera.

The illuminating can be strobed illuminating. In this embodiment, acquisition of said simultaneous images is synchronized to a strobe pulse to cause the simultaneous acquisition during an illumination period and the calculating motion data step can comprise processing the simultaneous images using a combination of segmentation, object features extraction and filtering.

A motion correcting tomography-based imaging system comprises a region of interest (ROI) to be imaged having at least three spaced apart optical markers thereon, at least one radiation detector for collecting radiation data from emitted from a radioactive isotope in said ROI or radiation data provided by the ROI attenuating radiation provided by an external radiation source, a first processor communicably connected to the radiation detector, and structure for rotating said ROI relative to the radiation detector. The motion correcting portion of the system comprises an at least one illumination source for illuminating the ROI, a first and a second camera for acquiring simultaneous images from the markers from different angles, and at least a second processor communicably connected to the first processor for calculating motion data comprising 3D position and orientation of the markers relative to an initial reference position, and motion correcting the radiation data, wherein motion corrected tomographic images are obtained from the motion correcting radiation data.

The tomography system can be a single photon emission computed tomography (SPECT) system. In a preferred embodiment, the markers are retro-reflective and the illuminating is aligned to be coaxial with an optical axis of the first and the second camera. The illuminating can be strobed illuminating, wherein acquisition of the simultaneous images is synchronized to a strobe pulse to cause the simultaneous acquisition during an illumination period. The at least one radiation detector preferably comprises a first and a second detector.

DETAILED DESCRIPTION

As noted above, high quality 3D images from conventional scanned data requires that the object or other structure to be imaged remain stationary during the scan. However, imaging live subjects that are free to move, such as animals (e.g. rats), presents difficulties during scans and significantly reduces the quality of the resulting 3D images. The invention corrects for this motion during the scan, thus improving the quality of 3D images obtained.

In one embodiment of the invention, a method for motion corrected tomographic imaging includes the steps of illuminating a region of interest (ROI), the ROI being part of an unrestrained live subject and having at least three spaced apart optical markers thereon. Simultaneous images are acquired from a first and a second camera of the markers from different angles. Motion data comprising 3D position and orientation (pose) of the markers relative to an initial reference position is then calculated from the simultaneous images. Using the motion data, corrected tomographic data is obtained from the ROI, wherein motion corrected tomographic images are obtained therefrom.

A preferred embodiment of the inventive method is now described. A pair of stereoscopically oriented cameras acquires a synchronized pair of frames so that each pair consists of two views of an arrangement of the markers at a certain point in time. For each stereo pair acquired by the cameras, an algorithm is used to locate the reflectors in each of the two images and calculate their position and orientation in three-dimensional space relative to the cameras. If the reflectors are affixed to a rigid body, then the configuration of the reflectors seen by the cameras can be directly translated to the relative pose of the body. The algorithms used to calculate pose in this method are fast enough that pose measurements can be performed in real time while the subject is undergoing a scan, allowing for immediate notification to the user if any tracking problems are encountered during the scan. The pose data is recorded to a file with a global timestamp and can later be merged with time-stamped SPECT scan data to correct for any motion and tomographically reconstruct an accurate depiction of the scanned area.

An exemplary system based on the invention been demonstrated for a single photon emission computed tomography (SPECT) scanner for performing awake animal imaging while compensating for the motion during the scan. SPECT is one of several nuclear imaging techniques. Generally, in nuclear imaging, a radioactive isotope is injected to, inhaled by or ingested by a subject, such as a patient or other subject. The isotope, provided as a radioactive-labeled pharmaceutical (radio-pharmaceutical) is chosen based on bio-kinetic properties that cause preferential uptake by different tissues. The gamma photons emitted by the radio-pharmaceutical are detected by radiation detectors outside the body, giving its spatial and uptake distribution within the body, with little trauma to the subject.

Although described relative to SPECT, the invention is in no way limited to SPECT. For example, the invention is applicable to other tomography, such as computed tomography (CT), or positron emission tomography (PET). The invention is also applicable to non-tomography-based scanned imagining, such as MRI or ultrasound. More generally, any application generally requiring 3D motion tracking of a living subject for positioning and correction can benefit from the invention.

FIG. 1 is a schematic diagram of an exemplary motion correcting SPECT imaging system 100. System 100 includes a motion correcting system 110 comprising IR LED sources 105 and 106 for illuminating a mouse burrow 112 having a live unrestrained mouse therein (not shown). The mouse has three spaced apart retro reflective optical markers attached to its head (not shown).

A minimum set of three markers is needed to measure both position and orientation. Although system 100 is described as having three (3) markers, any number of markers greater two (2) markers may be used. An algorithm for the calculation described below can fit three (3) or more markers to a model. Additional markers will generally improve system robustness. For example, if one or more markers become obscured, as long at least three (3) markers are observed, then a 3D measurement can still be made. While additional markers can improve the accuracy, additional run time is generally needed if more than three (3) markers are used.

It is preferred that the markers not be arranged in an equilateral triangle to eliminate rotational symmetry. This does not prevent the method from operating, but constrains the rotation.

For SPECT imaging, the mouse has a radioactive isotope injected into the region to be imaged. A first camera 116 and second camera 117 are provided for acquiring simultaneous images from the retro-reflective optical markers from different angles. High speed digital cameras are preferred for cameras 116 and 117, such as digital video cameras with frame rates generally exceeding about 15 frames/sec to capture live motion. An optical tracking PC 119 includes memory and a processor for calculating motion data comprising 3D position and orientation of the markers relative to an initial reference position. The initial reference position is arbitrary and can be selected as desired.

The illumination provide by LEDs 105 and 106 is shown as being coaxial (on-axis) with the optical axis of cameras 116 and 117. Half silvered minors 108 and 109 provide reflection of IR emitted by LEDs 105 and 106 onto the optical axis of cameras 116 and 117 and transmission of light from the mouse in burrow 112 along the optical axis of cameras 116 and 117. This arrangement optimizes illumination of the retro reflective markers and significantly increases marker intensity in the acquired images. The illumination is preferably strobed and the cameras 116 and 117 are simultaneously triggered to stop motion during exposure when acquiring simultaneous images from each camera.

System 100 includes a motion control PC 126 which includes memory and controls the relative motion of the mouse burrow 112 and SPECT detectors 128 and 129 in conjunction with a suitable gantry structure for rotating mouse burrow 112 (not shown). The radiation detectors can also include a specially designed collimator to acquire data from different projection views. System also includes a SPECT data acquisition PC 136 having memory. PC 136 receives the motion data comprising 3D position and orientation of the markers relative to an initial reference position from PC 119, and corrects the radiation data received for motion of mouse in the burrow 112 from detectors 128 and 129. Although described as having three (3) separate PCs, the invention can use one or more other processor and memory comprising devices for functions provided by PCs 119, 126 and 136. Although wired communications links are shown in FIG. 1, the invention is in no way limited to this arrangement. For example, communications can be optical or over the air (e.g. RF).

Figure 2:
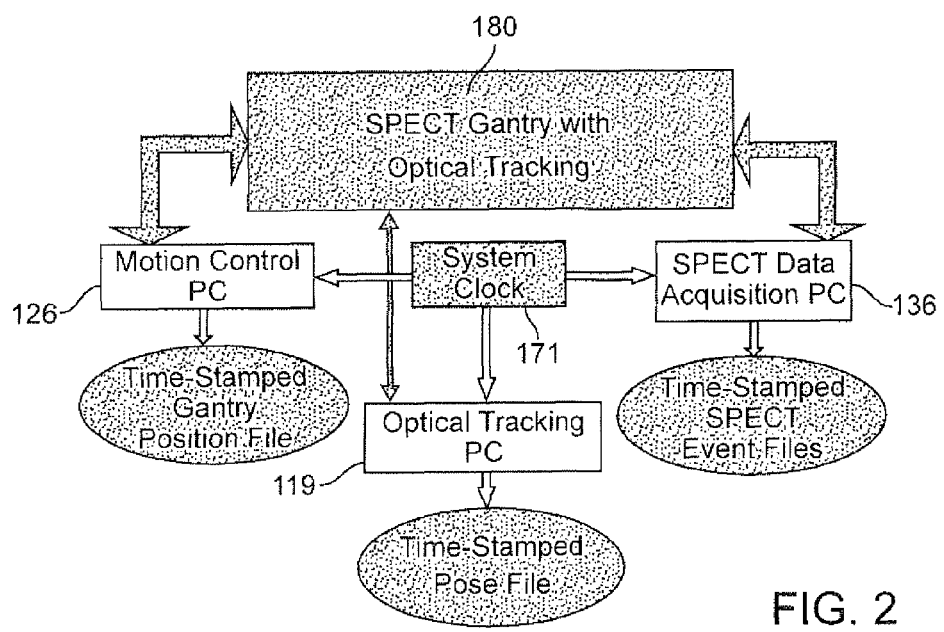
FIG. 2 shows a communication flow diagram for system components for system 100 shown in FIG. 1.

FIG. 2 shows a communication flow diagram based on system 100 shown in FIG. 1. A system clock 171 (common for the whole system) provides timing information to motion control PC 126, optical tracking PC 119, and SPECT data acquisition PC 136. The respective PCs time stamp image data obtained for storage therein. SPECT gantry 180 exchanges position information with PC 119.

Returning to the exemplary method, the first step in motion correction according to the invention is to measure the motion of the ROI to be imaged. The animal is generally confined but otherwise unrestrained, such as in a cylindrical burrow 112 with a hemispherical front. The burrow 112 is transparent to the illumination wavelength which in the case of the exemplary system is 830 nm from LEDs 105 and 106. This near IR wavelength is invisible to the animal and thus should cause no distraction. In addition, the burrow 112 is optically uniform so that external images of the animal can be made without significant distortion. Accurate measurement of position and orientation of the animal is required. The system must also process images fast enough to follow any motion smoothly without gaps especially when fast, jerky movements are encountered.

The inventive system and related method has been demonstrated to accurately measure head motion of mice using optical markers placed on the head. Cameras 116 and 117 shown in FIG. 1 were configured with optical CMOS cameras with 512 by 512 pixel resolution viewing the head from different angles to image the markers and then calculate the 3-D position and orientation of the markers with respect to an initial (reference) position.

The cameras 116 and 117 are preferably initially calibrated both intrinsically and extrinsically. Intrinsic calibration involves calculating the lens focal length, optical center, and lens distortion. Extrinsic calibration involves calculating the position and orientation of a calibration pattern with respect to the camera frame of reference. A stereo calibration is then performed to calculate the position and orientation of one camera with respect to the second. With this calibration and the measurement technique, measurement accuracies within 100 micrometers in position and 0.1 degrees in rotation can be obtained.

For the prototype SPECT system tested, system speed was limited by the CMOS cameras 116 and 117 and hardware in PC 119 to about 15 measurements/sec. Faster speeds can be obtained through higher frame rate cameras and higher performance PC hardware. However, this rate has been found sufficient to smoothly track mouse motion.

In a preferred embodiment, the below listed steps are preferably performed sequentially in computing the position and orientation of the ROI (the head of the animal).

1. Simultaneous images from each camera 116 and 117 of the head of the animal are acquired. The illumination is strobed to millisecond or sub-millisecond duration to freeze the motion of the ROI. The image acquisition from both cameras 116 and 117 is synchronized to the strobe pulse to cause the simultaneous acquisition during the illumination period.

2. Each image is processed to extract the marker positions by a combination of segmentation, object features extraction and filtering. An image processing reference for basic image segmentation (including region growing), feature extraction, and filtering is Digital Image Processing, Gonzalez and Woods, 2nd Edition, Prentice Hall, 2002. This step can use a region growing algorithm to segment the markers along with connected component analysis to extract shape and size parameters. Segmentation uses a region growing image thresholding method to separate the markers from the background. Connected component analysis identifies the separate markers, labels them, and calculates the location, size, aspect ratio, and other parameters for each marker. Due to reflections from the burrow 112, false segmentations can occur. The false segmentations are removed through a combination of shape and size filtering as well as model fitting described below. Filtering is performed on these geometric parameters to ensure that only true markers are identified since a marker has a hemispherical shape. For the special case where a reflection merges with a true marker, the contour can be analyzed for roundness and convexity to recover the true marker location.

3. Marker correspondence is performed using the fundamental matrix and epipolar line geometry. As a suitable reference for this step, see R. Hartley, A. Zisserman, Multiple View Geometry in Computer Vision, Cambridge: Cambridge University Press, 2000. The fundamental matrix is a 3 by 3 matrix that is an algebraic representation of epipolar geometry where epipolar geometry is the intrinsic projective geometry between two separate camera images. A property of epipolar line geometry is that corresponding points in stereo images line on the same epipolar line. The Hartley reference defines these terms. Use is made of this property in finding corresponding points and in accurately positioning the centroids of corresponding points to the nearest epipolar line. A 3-D point that is imaged by both cameras 116 and 117 lies on corresponding epipolar lines.

4. Marker locations are corrected to lie on nearest epipolar line to improve accuracy. The closest point on the epipolar line are computed from each image location.

5. The 3-D locations for each of the markers are now calculated. Based on known geometry the point of closest distance of the two 3-D lines from each camera image point and the optical center are computed. These are generally skew lines that do not intersect.

6. The markers are then fit to the model. Geometrical relationships and fitting error are used to choose best fit of markers to model. This fitting can occur even with additional false markers present. The fitting can use 3 or more marker points. The 3D coordinates of at least three markers are known in two reference frames: the camera reference frame and the model reference frame. What is unknown is the correspondence of the points between the reference frames. All valid geometric permutations of correspondence of points between the two frames are calculated using Horn's method (See B. Horn, "Closed-form solution of absolute orientation using unit quaternions," Journal of the Optical Society of America, 4, pp 629-642, April 1987.) This method calculates a 3D transformation and fitting error. The transformation that has the minimum fitting error and that satisfies the geometric constraints is selected. The geometric constraints require that the physical arrangement of points be the same in the two reference frames and that the model is facing the camera as an example.

7. The relative orientation of points between camera reference and model reference are then calculated. Horn's method (referenced above) is preferably used to calculate the relative orientation between the two reference frames.

8. The position and orientation of the ROI relative to an initial reference position is then calculated.

The invention thus provides a motion tracking system and related method which provides robust, reliable measurement of 3D position and orientation of a ROI where motion is present and where point features can be located in optical images. The invention is fast, able to monitor and correct image data for motion, including motion that is neither smooth or continuous. Accurate position measurements better than 0.1 mm have been made within a volume of a 75 mm cube. Moreover, objects within a transparent enclosure can be measured and where only a narrow angle access to the object view is limited due to obstructions.

The invention can benefit any application generally requiring 3D motion tracking of a living subject for positioning and correction. Motion tracking system according to the invention can thus be used in a wide variety of systems which require exacting alignment, particularly when the region of interest is moving (or can move) during the measurement or other procedure. Significantly, using optical methods according to the invention to track the position of the animal during a scan, the physiology of the animal can be kept free from physical and chemical effects that are otherwise necessary for high quality imaging which can interfere with the control of conventional pharmaceutical screening processes.

As noted above, the invention can be applied to SPECT, other tomography, such as computed tomography (CT) and positron emission tomography (PET), as well as non-tomography-based scanned imagining, such as MRI or ultrasound. The invention can be integrated into new systems as well as be used to retrofit existing systems.

EXAMPLES

It should be understood that the Examples described below are provided for illustrative purposes only and do not in any way define the scope of the invention.

Figure 3A:
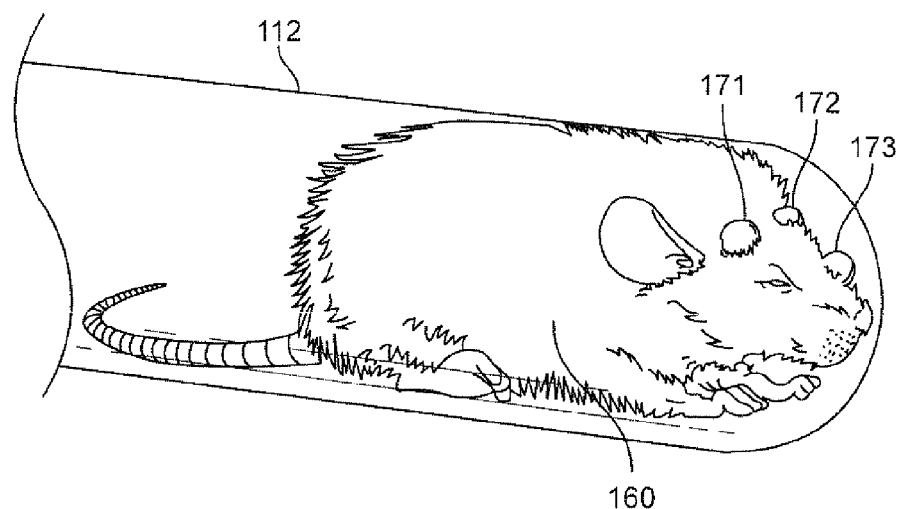
Figure 3B:
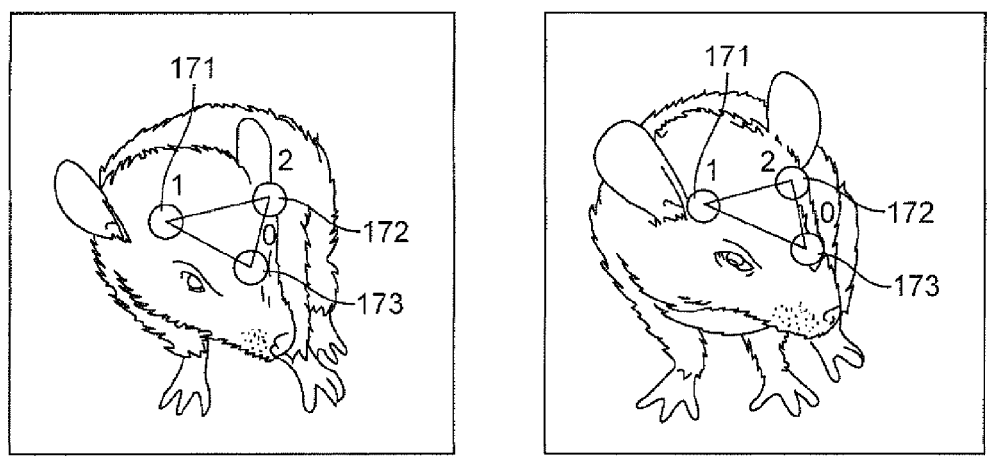
FIG. 3(b) shows a scanned image of the mouse with the retro reflectors from each camera and with tracking enabled. The markers are outlined and numbered showing that they have been segmented and that correspondence has been determined. In this depiction, the lines between the markers indicates that successful model fitting has been done and that a full 3D transformation has been calculated between the camera reference frame and the model reference frame.

FIG. 3(a) shows a scanned image of a mouse 160 fitted with three optical retro-reflective markers 171, 172 and 173 on its head in a burrow 112. Images of the mouse with the retro reflectors from each camera and with tracking enabled are shown in FIG. 3(b). Tracking is shown by lines connecting the center of each marker 171-173. Also visible are reflections off the glass tube enclosure that have been ignored. The markers are outlined and numbered showing that they have been segmented and that correspondence has been determined. In this depiction, the lines between the markers 171-173 indicates that successful model fitting has been performed and that a full 3D transformation has been calculated between the camera reference frame and the model reference frame.

This invention can be embodied in other forms without departing from the spirit or essential attributes thereof and, accordingly, reference should be had to the following claims rather than the foregoing specification as indicating the scope of the invention.

We claim:

1. A method for generating motion corrected tomographic images, comprising the steps of:
    illuminating a region to of interest (ROI) to be imaged being part of an unrestrained live subject located in a burrow and having at least three spaced apart optical markers thereon;
    acquiring first and second sets of simultaneous images of said markers, wherein both the first and the second set of simultaneous images are acquired from a first and a second camera from different angles;
    determining an initial reference position of said markers using said first set of simultaneous images;
    calculating motion data using said second set of simultaneous images, said motion data comprising 3D position and orientation of said markers in the second set of simultaneous images relative to said initial reference position of said markers, and
    motion correcting tomographic data obtained from said ROI using said motion data, wherein motion corrected tomographic images are obtained, wherein said calculating motion data step comprises processing said second set of simultaneous images using segmentation, followed by object features extraction and filtering, said segmentation comprising removing reflections from a surface of the burrow with size and shape filtering.

2. The method of claim 1, wherein said ROI is provided by an unrestrained awake animal.

3. The method of claim 2, wherein during said method said animal is disposed in an confinement volume which is optically transparent to a wavelength of radiation used for said illuminating.

4. The method of claim 1, wherein said tomographic images are single photon emission computed tomography (SPECT) images.

5. The method of claim 1, wherein said markers are retro-reflective and said illuminating is aligned to be coaxial with an optical axis of said first and said second camera.

6. The method of claim 1, wherein said illuminating is strobed illuminating.

7. The method of claim 6, wherein acquisition of said simultaneous images is synchronized to a strobe pulse to cause the simultaneous acquisition during an illumination period.

8. A motion correcting tomography-based imaging system, comprising:
    a region of interest (ROI) to be imaged having at least three spaced apart optical markers thereon;
    at least one radiation detector for collecting radiation data emitted from a radioactive isotope in said ROI or radiation data provided by said ROI attenuating radiation provided by an external radiation source, and a first processor communicably connected to said radiation detector, and structure for rotating said ROI relative to said radiation detector, and a motion correcting system, comprising:
    at least one illumination source for illuminating said ROI;
    a burrow in which said ROI will be located;
    a first and a second camera for acquiring simultaneous images from said markers from different angles, and
    at least a second processor communicably connected to said first processor for calculating motion data and motion correcting said radiation data, wherein motion corrected tomographic images are obtained from said motion correcting radiation data, said first processor determining an initial reference position of said markers using a first set of simultaneous images and calculating said motion data using a second set of simultaneous images, wherein said motion data comprises 3D position and orientation of said markers in the second set of simultaneous images relative to said initial reference position, and wherein calculating said motion data comprises processing said second set of simultaneous images using segmentation followed by, object features extraction and filtering, said segmentation comprising removing reflections from a surface of the burrow with size and shape filtering.

9. The system of claim 8, wherein said system is a single photon emission computed tomography (SPECT) system.

10. The system of claim 9, wherein said markers are retro-reflective and said illuminating is aligned to be coaxial with an optical axis of said first and said second camera.

11. The system of claim 1, wherein said illuminating is strobed illuminating.

12. The system of claim 11, wherein acquisition of said simultaneous images is synchronized to a strobe pulse to cause the simultaneous acquisition during an illumination period.

13. The system of claim 9, wherein said at least one radiation detector comprises a first and a second detector.

* * * * *